(12) United States Patent
Cruz

(10) Patent No.: US 9,968,506 B2
(45) Date of Patent: May 15, 2018

(54) THERAPEUTIC SYSTEM AND METHOD FOR FLEXING AND EXTENDING METACARPAL AND PHALANGEAL JOINTS

(71) Applicant: Luis Cruz, Miami, FL (US)

(72) Inventor: Luis Cruz, Miami, FL (US)

( * ) Notice: Subject to any disclaimer, the term of this patent is extended or adjusted under 35 U.S.C. 154(b) by 444 days.

(21) Appl. No.: 14/809,178

(22) Filed: Jul. 25, 2015

(65) Prior Publication Data

US 2017/0020763 A1  Jan. 26, 2017

(51) Int. Cl.
| | | |
|---|---|---|
| *A61H 1/00* | (2006.01) | |
| *A61H 1/02* | (2006.01) | |
| *A61H 5/00* | (2006.01) | |
| *A61F 7/02* | (2006.01) | |
| *A61F 7/00* | (2006.01) | |

(52) U.S. Cl.
CPC .............. *A61H 1/0288* (2013.01); *A61F 7/02* (2013.01); *A61F 2007/0037* (2013.01); *A61F 2007/0233* (2013.01); *A61H 2201/0207* (2013.01); *A61H 2201/0214* (2013.01); *A61H 2205/067* (2013.01)

(58) Field of Classification Search
CPC ......... A63B 21/00; A63B 23/00; A63B 23/12; A61H 1/02; A61H 2005/067; A61H 2201/02; A61H 2201/0214; A61F 2007/02; A61F 2007/00; A61F 7/02
See application file for complete search history.

(56) References Cited

U.S. PATENT DOCUMENTS

| | | | | |
|---|---|---|---|---|
| 3,741,207 A | * | 6/1973 | Fuson | A61F 13/104 128/879 |
| 4,541,127 A | * | 9/1985 | Gould | A63B 71/143 2/161.1 |
| 4,654,895 A | * | 4/1987 | Peters | A41D 19/0017 2/161.1 |
| 4,671,258 A | * | 6/1987 | Barthlome | A61H 1/0288 128/DIG. 20 |
| 4,691,387 A | * | 9/1987 | Lopez | A41D 19/01547 2/159 |
| 5,004,231 A | * | 4/1991 | Alread | A63B 21/4019 2/159 |
| 5,184,815 A | * | 2/1993 | Maddox | A63B 69/0002 2/161.1 |
| 5,500,956 A | * | 3/1996 | Schulkin | A63B 71/148 2/159 |

(Continued)

*Primary Examiner* — Garrett Atkinson
(74) *Attorney, Agent, or Firm* — Ruben Alcoba, Esq.

(57) ABSTRACT

A therapeutic system and method flexes, extends, and exercises the metacarpal and phalangeal joints of an affected hand. The system comprises a therapeutic glove that receives an affected hand and adjustably applies movement to the fingers and thumb in a first forward direction to form a flexion position, and a second rearward direction to form an extension position. The position of the fingers and thumb as well as the amount of pressure applied is controlled by manipulating restraining members to pull and restrain the fingers and thumb and then attaching to a corresponding body and wrist portion on the glove. The extent of the pulling, including the pressure applied to the metacarpal and phalangeal joints, is fixed, adjustable, and easily releasable. A secondary therapeutic glove compensates for the tactile perception feedback from an unaffected hand. A therapeutic pain relief modality is applied prior to donning the glove.

19 Claims, 3 Drawing Sheets

(56) References Cited

U.S. PATENT DOCUMENTS

| | | | | |
|---|---|---|---|---|
| 5,683,335 A * | 11/1997 | Groves | A43B 19/005 | 482/105 |
| 6,049,910 A * | 4/2000 | McCarter | A63B 71/148 | 2/161.1 |
| 6,430,750 B1 * | 8/2002 | Tourbier | A41D 19/001 | 2/159 |
| 6,539,551 B1 * | 4/2003 | Jones, Jr. | A63B 69/3608 | 2/159 |
| 6,604,244 B1 * | 8/2003 | Leach | A41D 19/0055 | 15/227 |
| 7,051,377 B1 * | 5/2006 | Milner | A41D 19/01547 | 2/159 |
| 7,063,646 B1 * | 6/2006 | Slimi | A63B 22/14 | 482/141 |
| D587,409 S * | 2/2009 | Raymond | D29/117.2 | |
| 8,092,411 B2 * | 1/2012 | Betcher | A61F 5/0118 | 128/878 |
| 2004/0226074 A1 * | 11/2004 | Taira | A41D 13/0587 | 2/159 |
| 2008/0263747 A1 * | 10/2008 | DeBlasis | A41F 1/06 | 2/161.1 |
| 2011/0118635 A1 * | 5/2011 | Yamamoto | A61H 1/02 | 601/5 |
| 2011/0126342 A1 * | 6/2011 | Bautista | A63B 71/143 | 2/161.1 |
| 2012/0061371 A1 * | 3/2012 | Broom | A63C 11/222 | 219/211 |
| 2012/0167272 A1 * | 7/2012 | Scaff | A61F 5/0118 | 2/160 |
| 2013/0227760 A1 * | 9/2013 | Mahon | A41D 19/01 | 2/160 |
| 2015/0289576 A1 * | 10/2015 | Woody | A41D 19/0024 | 2/16 |
| 2015/0374053 A1 * | 12/2015 | Mahon | A41D 19/01 | 2/160 |

\* cited by examiner

US 9,968,506 B2

THERAPEUTIC SYSTEM AND METHOD FOR FLEXING AND EXTENDING METACARPAL AND PHALANGEAL JOINTS

BACKGROUND

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The present invention is directed a therapeutic system and method for flexing, extending, and generally exercising the metacarpal phalangeal joints of an affected hand. The system comprises a therapeutic glove that is configured to receive an affected hand and adjustably apply movement to the fingers and thumb in a first direction to form a flexion position, and a second direction to form an extension position.

The inventor is a therapist who works with patients having adversely affected and deformed hands. Specifically, the inventor was familiar with problems such as: hemiplegia, hemi paresis, trigger finger, complex regional pain syndrome, hand surgeries, developmental disabilities, spinal cord injuries, and other affections similarly limiting the normal functioning of the hands. Through years of experience, the inventor knew that these types of therapy patients may benefit more from bilateral proximal training, rather than from unilateral task oriented training.

The inventor recognized a problem in that the patients had difficulty gripping objects for daily activities, such as eating and personal hygiene. The patients also could not lift weights to develop their upper extremities. This required a flexion position for the metacarpal and phalangeal joints of an affected hand. The inventor also saw that patients who had cramping issues required the metacarpal and phalangeal joints to be stretched into an extension position, opposite of the flexion position.

Through additional research, the inventor learned that favorable therapies would result in the following: therapeutic exercises like passive flexion and extension of the fingers; facilitating effective grasping of activity of daily living utensils by the affected hands; facilitating effective grasping of therapeutic weights, therapeutic devices, and locomotion devices by the affected hands; facilitating the therapeutic use of static and dynamic hand splints; assisting in strengthening of affected upper extremities; assisting in performing isometric and isotonic therapeutic exercises of the upper extremities; assisting with stretching fingers with minimal pain on patients with complex regional pain syndrome; and assisting with flexion and extension of fingers of patients affected by hemiplegia, hemiparesis finger fractures, hand surgery, trigger finger, upper extremity spasticity, and contractures as seen on cerebral palsy and Spina Bifida.

To address these needs, the inventor initially developed a dynamic hand flexor-extensor assistive glove. The glove was dimensioned dot receive variously sized hands and maintain separation between the fingers and thumb. The glove included a body portion that defined the hand, a wrist portion that enabled entry of and disengagement of the hand, and a plurality of tubular finger elements that received the fingers and thumb from the hand.

Through experimentation, the inventor manipulated the glove, by adding elongated retraining members to the termini of the tubular finger members. The restraining members could be pulled in a forward or backward direction to exercise the metacarpal and phalangeal joints of the affected hand.

However, the inventor saw that the tubular finger elements would not stay in place. The inventor decided to add hook and loop fastening mechanisms to each section of the glove. The restraining members also integrated hook and loop fasteners. In this manner, the restraining member could be pulled and then held into place with a corresponding portion of the glove, as therapy dictated.

For the foregoing reasons, there is a therapeutic system and method for flexing, extending, and generally exercising the metacarpal and phalangeal joints of an affected hand.

Therapy systems and methods for affected hands have been utilized in the past; yet none with the characteristics of the present invention. See U.S. Pat. Nos. 5,667,466; 4,618, 850; and 20140287882.

For the foregoing reasons, there is a therapeutic system and method flexes, extends, and exercises the metacarpal phalangeal and joints of an affected hand. The system comprises a therapeutic glove that receives an affected hand and adjustably applies movement to the fingers and thumb in a first forward direction to form a flexion position, and a second rearward direction to form an extension position. The position of the fingers and thumb as well as the amount of pressure applied is controlled by manipulating restraining members to pull and restrain the fingers and thumb and then attaching to a corresponding body and wrist portion on the glove. The extent of the pulling, including the pressure applied to the metacarpal and phalangeal joints, is fixed, adjustable, and easily releasable.

SUMMARY

The present invention describes a therapeutic system and method for flexing, extending, and generally exercising the metacarpal and phalangeal joints of an affected hand. The system comprises a therapeutic glove that is configured to receive an affected hand and adjustably apply movement to the fingers and thumb in a first direction to form a flexion position, and a second direction to form an extension position. The position of the fingers and thumb as well as the amount of pressure applied to the fingers and thumb may be controlled.

The controlled manipulation of the fingers and thumb enables a therapist to create customized treatments for treating the metacarpal and phalangeal joints in the affected hand. This displacement of the fingers and thumb assists with passive flexion and extension of the metacarpal phalangeal joints for the affected hand. In some embodiments, the system may further include a secondary therapeutic glove that is configured to compensate the tactile perception feedback from an unaffected hand.

The therapeutic glove is configured to fit over the affected hand, and is secured thereto through a hook and loop fastening mechanism, enabling a user to accomplish various manipulations and exercises with the benefit of a plurality of restraining members that pull and restrain the fingers and thumb of the hand. The extent of the pulling, including the pressure applied to the metacarpal and phalangeal joints, is fixed, adjustable, and easily releasable.

In one embodiment, the hook and loop fastening mechanism forms a substantial portion of the surface of the glove. The hook and loop fastening mechanism restrains the glove, including the fingers and the thumb contained therein, at a desired position. In this manner, a desired amount of pressure is induced to each finger and thumb while pulling to attach them to a corresponding hook and loop fastener.

In one embodiment, the therapeutic glove, when donned, enables the fingers and thumb to be pulled and restrained in a first direction to form a flexion position. From the flexion position, the hand may grip an object and the metacarpal and phalangeal joints may be flexed in a therapeutic manner. In another embodiment, the therapeutic glove, when donned, enables the fingers and thumb to be pulled and restrained in a second direction to form an extension position. From the extension position, the metacarpal and phalangeal joints may be stretched, as therapeutic needs of the affected hand require.

In some embodiments, each finger and thumb may be pulled in opposite directions relative to each other while inside the therapeutic glove. For example, the thumb and the forefinger is pulled in the first direction to form the flexion position, while the middle finger, index finger, and pinky are pulled in the second direction to form the extension position. The therapeutic needs of the hand indicate the directional and tension applied to the fingers and thumb.

In some embodiments, the affected hand is treated through pain relief modality, which may include, without limitation, heat, paraffin, myofascial release, hot or ice packs, and gently stretching. The pain relief modality is applied before receiving the therapeutic benefits of the therapeutic glove. Further, the secondary therapeutic glove, as discussed above, is configured to fit over the unaffected hand, and is secured thereto, enabling a user to compensate the tactile perception feedback from an unaffected hand.

In some embodiments, the therapeutic system comprises a glove that is configured to receive the affected for therapeutic manipulations of the fingers and thumb. The glove comprises a body portion that is shaped and dimensioned to receive a hand. The body portion includes a body dorsal side and a body palm side. The body dorsal side is configured to engage the back side of a hand. The palm side is configured to engage the palm of a hand. The body dorsal side includes a body dorsal fastener. The body dorsal fastener may include a hook and loop fastener strip. The body palm side includes a body palm fastener. The body palm fastener may include a hook and loop fastener.

The therapeutic glove further comprises a wrist portion having an opening to enable passage of the hand. The wrist portion includes a wrist dorsal side and a wrist palm side. The wrist dorsal side has a wrist dorsal fastener. The wrist dorsal fastener may include a hook and loop fastener. The wrist palm side forms the opposite side to the wrist dorsal side. The wrist palm side has a wrist palm fastener. The wrist palm fastener may include a hook and loop fastener.

The therapeutic glove further comprises a plurality of tubular finger elements that are configured to receive a plurality of digits and at least partially extend or flex the digits. The digits may include the four fingers and the thumb.

The therapeutic system further comprises a plurality of restraining members disposed to extend from the terminus of the plurality of tubular finger elements. The restraining members include a restraining member dorsal fastener. The restraining member dorsal fastener may include a hook and loop fastener that is complimentary to the body dorsal fastener and the wrist dorsal fastener. The restraining members further include a restraining member palm fastener.

The restraining member palm fastener may include a hook and loop fastener that is complimentary to the body palm fastener and the wrist palm fastener. The hook and loop fastening mechanism of the restraining member dorsal fastener and the restraining member palm fastener enable detachable and quick attachment to the corresponding body dorsal fastener and the wrist dorsal fastener. The pressure that is applied to the fingers and thumb are also more easily controlled through the use of a hook and loop fastening mechanism.

Thus, pulling the restraining members in a first direction and joining the restraining member dorsal fastener to the complimentary dorsal fasteners of the body portion and wrist portion forms a flexion position. The flexion position enables the hand to grip an object and the metacarpal phalangeal joints to flex. Conversely, pulling the restraining members in a second direction and joining the restraining member palm fastener to the complimentary palm fasteners of the body portion and wrist portion forms an extension position. The extension position enables the metacarpal and phalangeal joints of a hand to stretch.

One objective of the present invention is to provide a therapeutic glove that enables therapeutic exercises like passive flexion and extension of the fingers.

Another objective of the present invention is to facilitate effective grasping of therapeutic weights, therapeutic devices, and locomotion devices by the affected hands.

Another objective of the present invention is to facilitate effective grasping of utensils by the affected hands.

Yet another objective of the present invention is to facilitate the therapeutic use of static and dynamic hand splints.

Yet another objective is to assist in strengthening of affected upper extremities.

Yet another objective of the present invention is to assist in performing isometric and isotonic therapeutic exercises of the upper extremities.

Yet another objective is to assist with stretching fingers with minimal pain on patients with complex regional pain syndrome.

Yet another objective of the present invention is to assist with flexion and extension of the fingers of patients affected by hemiplegia, hemiparesis finger fractures, hand surgery, trigger finger, upper extremity spasticity, and contractures as seen on cerebral palsy and Spina Bifida.

Yet another objective is to provide a hook and loop fastening mechanism that enables adjustable tensioning of the fingers and thumb in the flexion and extension positions.

Yet another objective is to provide a hook and loop fastening mechanism that reinforces such attachment for safety to prevent detachment of the restraining members and to firmly secure the glove to the hand.

Yet another objective of the present invention is to provide a secondary glove to compensate the tactile perception feedback from the unaffected hand.

Yet another objective of the present invention is to provide a secondary glove to compensate the tactile perception feedback from the unaffected hand.

DRAWINGS

These and other features, aspects, and advantages of the present invention will become better understood with regard to the following description, appended claims, and drawings where:

DESCRIPTION

The present invention is directed to a therapeutic system and device 100 and method 200 that exercises the metacarpal and phalangeal joints of an affected hand. The therapeutic system 100 and method 200 enables the fingers and thumb to be flexed, extended, and manipulated into a gripping form, so as to provide therapeutic exercises to the metacarpal and phalangeal joints of the affected hand. This displacement of the fingers and joints assists with passive flexion and extension of the metacarpal and phalangeal joints of the affected hand.

Those skilled in the art will recognize that an affected hand that may require such manipulations of the metacarpal and phalangeal joints are therapy patients who suffer from conditions limiting the use of upper extremities. Among these conditions include: hemiplegia, hemi paresis, trigger finger, complex regional pain syndrome, hand surgeries, developmental disabilities, spinal cord injuries, and other affections similarly limiting the normal functioning of the hands.

Generally, these types of therapy patients may benefit more from bilateral proximal training, as the present invention enables, rather than from unilateral task oriented training. Thus, the therapeutic system 100 and method 200 allows these types of therapy patients to securely grasp and hold different items to facilitate exercising the upper extremities and to ambulate using assistive devices.

Figure 1:
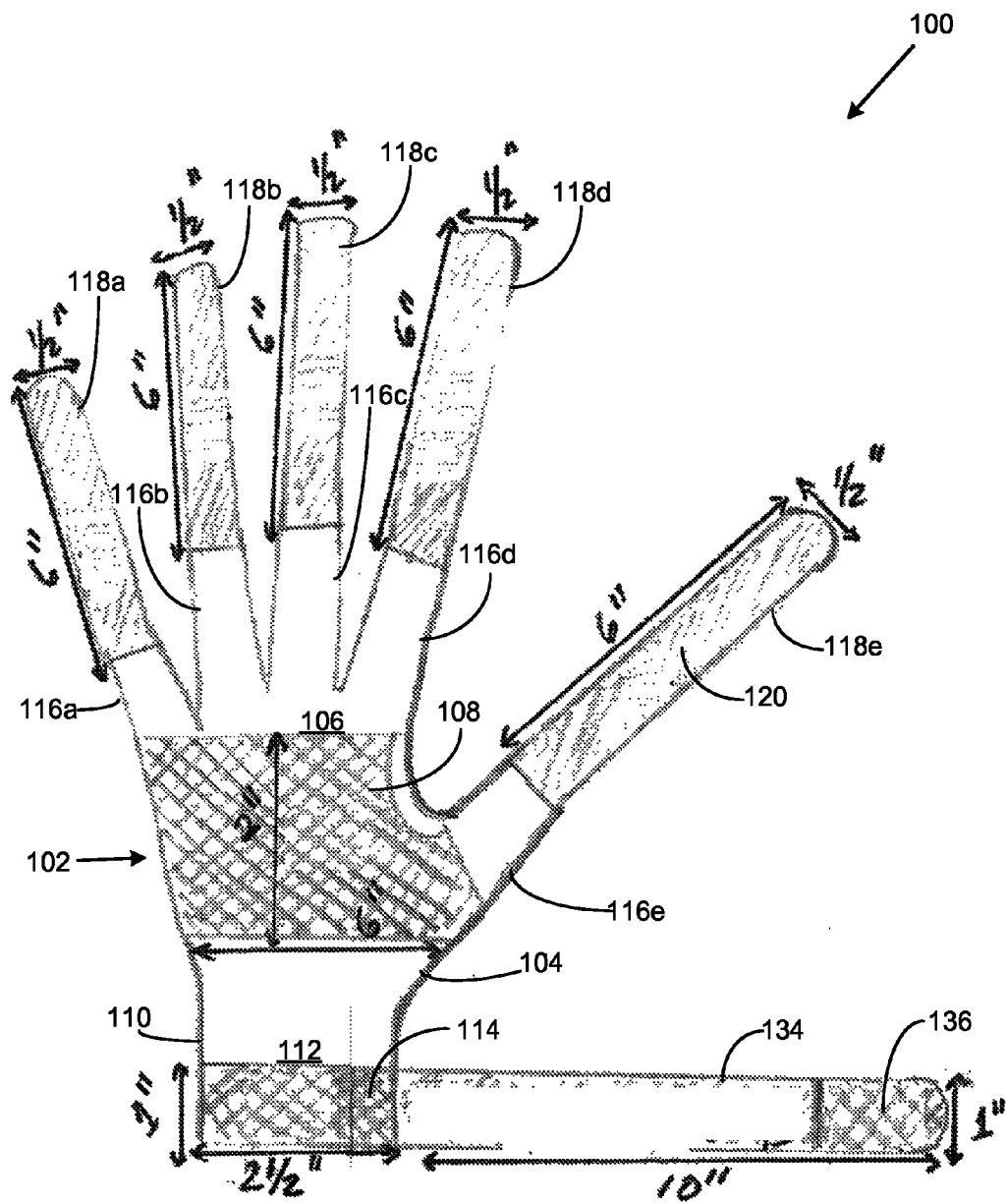
FIG. 1 is a top view of an exemplary therapeutic glove from a dorsal side.

As referenced in FIG. 1, the therapeutic system 100 comprises a glove 102 that is configured to receive an affected hand and adjustably apply movement to the fingers and thumb in a first direction to form a flexion position, and a second direction to form an extension position. The position of the fingers and thumb as well as the amount of pressure applied to the fingers and thumb may be controlled from both the flexion and extension positions. Consequently, the controlled manipulation of the fingers and thumb enables a therapist to create customized treatments for treating the metacarpal phalangeal joints in the affected hand.

The glove 102 is configured to fit over the affected hand, and is secured thereto through a hook and loop fastening mechanism, enabling a user to accomplish various manipulations and exercises with the benefit of a plurality of restraining members 118a-e that pull and restrain the fingers and thumb of the hand. The extent of the pulling, including the pressure applied to the metacarpal and phalangeal joints, is fixed, adjustable, and easily releasable. For example, the fingers are pulled in a first direction until the threshold of pain is reached, at which point the fingers are fixed at that position by fastening through a hook and loop fastening mechanism.

In one embodiment, the hook and loop fastening mechanism forms a substantial portion of the surface of the glove 102. The hook and loop fastening mechanism restrains the glove 102, including the fingers and the thumb contained therein, at a desired position. In this manner, a desired amount of pressure is induced to each finger and thumb while pulling to attach them to a corresponding hook and loop fastener.

In one embodiment, the glove 102, when donned, enables the fingers and thumb to be pulled and restrained in a first direction to form a flexion position. From the flexion position, the hand may grip an object and the metacarpal and phalangeal joints may be flexed in a therapeutic manner. The flexion position also enables the therapy patient to perform daily activities, such as eating and combing, securely grasping and hold therapeutic devices, lifting weights to strengthen the upper extremities.

In another embodiment, the glove 102 enables the fingers and thumb to be pulled and restrained in a second direction to form an extension position. From the extension position, the metacarpal and phalangeal joints may be stretched, as therapeutic needs of the affected hand require. The extension position is especially effective for affected hands that cramp. Consequently, therapeutic patients with hand contractures may stretch fingers and adopt anatomic positions without the use of other types of splints, or repositioning of the fingers when using static or dynamic hands splints.

In some embodiments, each finger and thumb may be pulled in opposite directions relative to each other while inside the glove 102. For example, the thumb and the forefinger is pulled in the first direction to form the flexion position, while the middle finger, index finger, and pinky are pulled in the second direction to form the extension position. The therapeutic needs of the hand indicate the directional and tension applied to the fingers and thumb.

In some embodiments, the affected hand is treated through pain relief modality, which may include, without limitation, heat, paraffin, myofascial release, hot or ice packs, and gently stretching. The pain relief modality is applied before receiving the therapeutic benefits of the glove 102. One advantage provided by the therapeutic system 100 is that donning the glove 102 immediately after warming the affected hand contributes to maintaining the warm temperature for a longer period of time. This application of the glove 102 facilitates longer and more effective therapeutic exercises session.

Further, the secondary therapeutic glove is configured to fit over an unaffected hand, and is secured thereto. The secondary therapeutic glove is configured to compensate the tactile perception feedback from an unaffected hand.

As referenced in FIG. 1, the glove 102 comprises a body portion 104 that is configured to receive the affected hand. The body portion 104 includes a body dorsal side 106 and a body palm side 122. The glove 102 is generally resilient, and dimensioned to fit a variety of hand sizes. In one embodiment, the glove 102 includes a small size, a medium size, and a large size. In this manner, the glove 102 fits snugly onto the affected hand, so as to inhibit shifting around while performing exercises that require lifting and pulling. Suitable materials for the glove 102 may include, without limitation, a breathable fabric, cotton, neoprene, rubber, and synthetic fabrics. The body portion 104 of the glove 102 may also be fabricated to wick away sweat.

Figure 2:
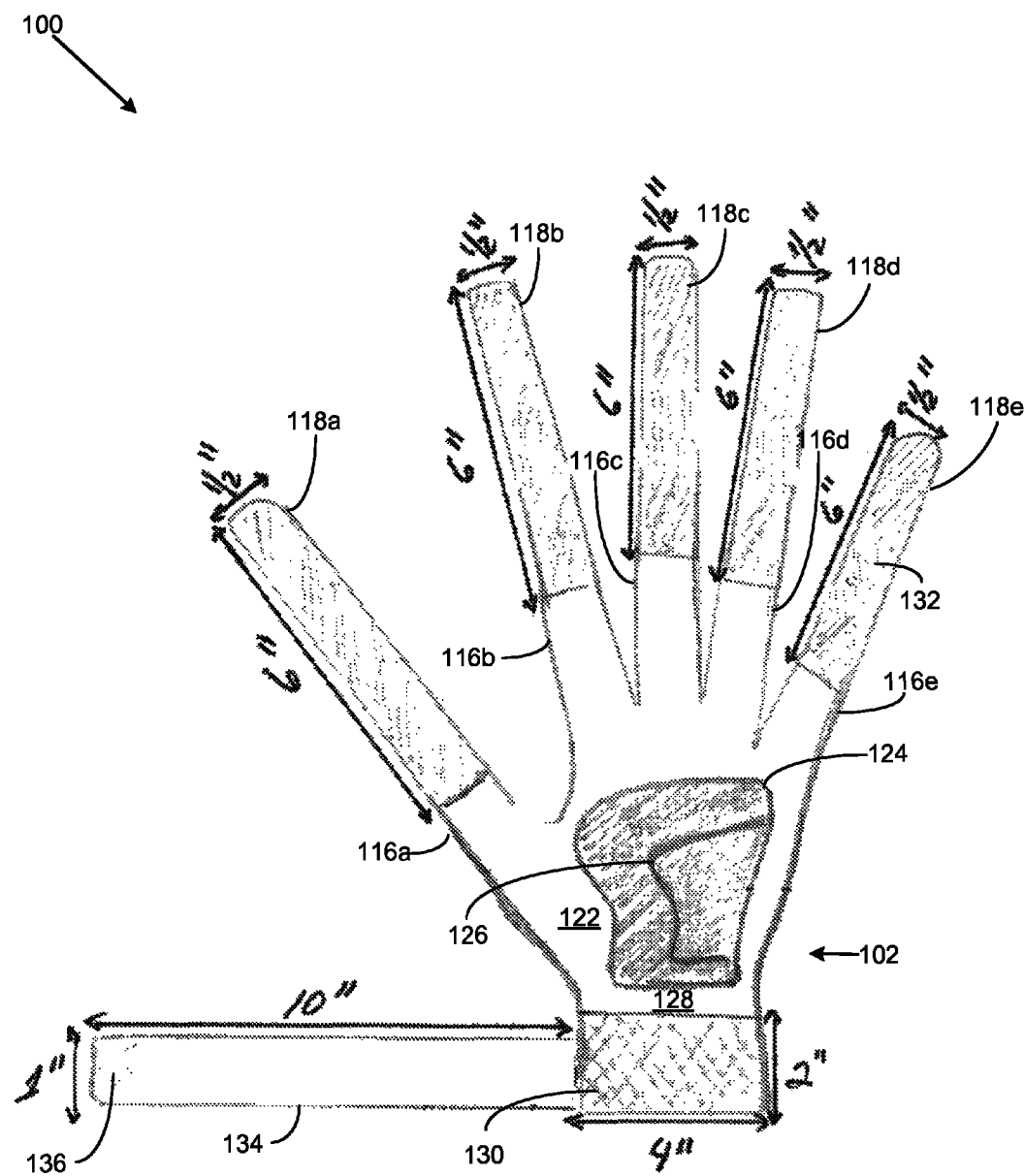
FIG. 2 is a top view of an exemplary therapeutic glove from a palm side.

The body dorsal side 106 of the glove 102 is configured to engage the back of the affected hand (FIG. 1). The body dorsal side 106 includes a body dorsal fastener 108. The body dorsal fastener 108 may include a panel of a hook and loop fastener about 6" wide and 2" long. The body palm side 122 of the glove 102 is configured to engage the palm of the affected hand (FIG. 2). The body palm side 122 includes a body palm fastener 124. The body palm fastener 124 may include a panel of a hook and loop fastener about 6" wide and 2" long. In some embodiments, a leather padding 126 hingedly covers the body palm fastener 124.

As illustrated in FIGS. 1 and 2, the therapeutic glove 102 further comprises a wrist portion 110 having an opening to enable passage of the affected hand. In one embodiment, the wrist portion 110 is about 2" wide. The wrist portion 110 includes a wrist dorsal side 112 and a wrist palm side 128. The wrist dorsal side 112 has a wrist dorsal fastener 114, which may include a strip of a hook and loop fastener about 4" long and 2" wide. The wrist palm side 128 forms the opposite side to the wrist dorsal side 112. The wrist palm side 128 has a wrist palm fastener 130, which may include a strip of a hook and loop fastener about 4" long and 2" wide. In some embodiments, a wrist strap 134 extends from the wrist portion 110 to wrap around the wrist. The wrist strap 134 terminates at a wrist strap fastener 136 that detachably attaches to the wrist dorsal fastener 114 and the wrist palm fastener 130. This fastening configuration helps to securely maintain the affected hand in the glove 102 during therapy.

Looking back at FIG. 1, the therapeutic glove 102 also comprises a plurality of tubular finger elements 116a-e that are configured to receive a plurality of digits and at least partially extend or flex the digits. The digits may include the four fingers and the thumb. The tubular finger elements 116a-e correspond to the fingers and thumb of the affected hand. In one embodiment, four tubular finger elements correspond to the forefinger, the middle finger, the index finger, and the pinky.

The therapeutic system 100 further comprises a plurality of restraining members 118a-e disposed to extend from the terminus of the plurality of tubular finger elements 116a-e. The restraining members 118a-e include a restraining member dorsal fastener 120. The restraining member dorsal fastener 120 may include a hook and loop fastener that is complimentary to the body dorsal fastener 108 and the wrist dorsal fastener 114. The restraining member dorsal fastener 120 may include a strip of a hook and loop fastener about 6" long and ½" wide.

The restraining members 118a-e further include a restraining member palm fastener 132. The restraining member palm fastener 132 may include a hook and loop fastener that is complimentary to the body palm fastener 124 and the wrist palm fastener 130. The restraining member palm fastener 132 may include a strip of a hook and loop fastener about 6" long and ½" wide. The hook and loop fastening mechanism of the restraining member dorsal fastener 120 and the restraining member palm fastener 132 enable detachable and quick attachment to the corresponding body dorsal fastener 108 and the wrist dorsal fastener 114. The pressure that is applied to the fingers and thumb in the first and second directions is more easily controlled through the use of a hook and loop fastening mechanism.

Thus, pulling the restraining members 118a-e in the first direction and joining the restraining member dorsal fastener 120 to the complimentary dorsal fasteners 108, 114 of the body portion 104 and wrist portion 110 forms a flexion position. The flexion position enables the hand to grip an object and the metacarpal and phalangeal joints to flex. The amount of force applied while pulling the restraining members 118a-e dictates the pressure that is applied onto the metacarpal and phalangeal joints of the affected hand.

Conversely, pulling the restraining members 118a-e in a second direction and joining the restraining member palm fastener 132 to the complimentary palm fasteners 124, 130 of the body portion 104 and wrist portion 110 forms an extension position. The extension position enables the metacarpal and phalangeal joints of a hand to stretch. In one possible embodiment, therapeutic session with the glove 102 may be for no less than twenty minutes up to sixty minutes, and a recommended schedule is one or two times daily for these durations.

Figure 3:
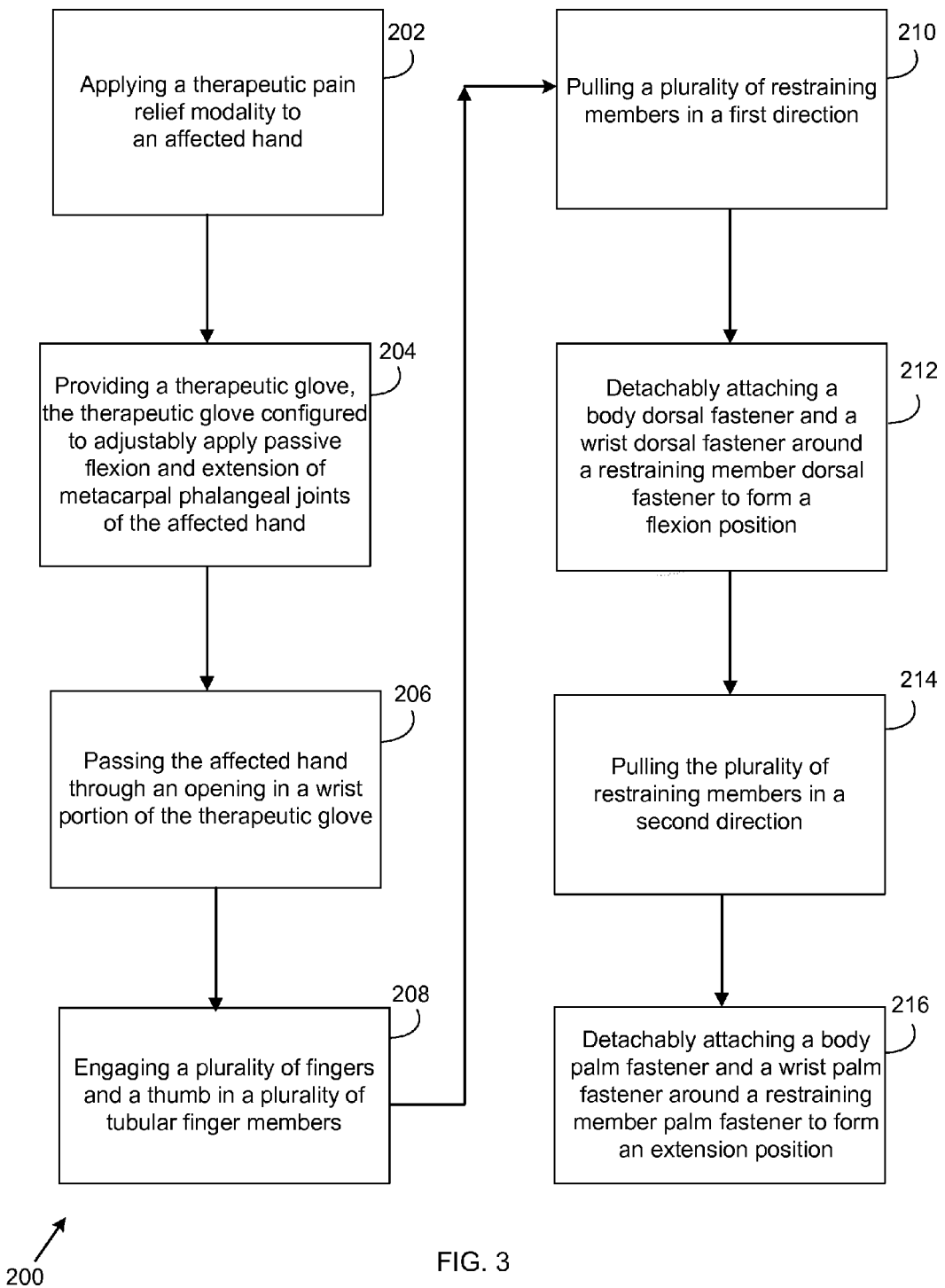
FIG. 3 is a flowchart diagram of an exemplary method for flexing and extending the metacarpal and phalangeal joints of an affected hand.

FIG. 3 illustrates a flowchart diagram of an exemplary method 200 for flexing and extending the metacarpal and phalangeal joints of an affected hand. The method 200 enables various manipulations with a therapeutic glove 102. The glove 102 is configured to receive an affected hand and adjustably apply movement to the fingers and thumb in a first forward direction and a second rearward direction. The position of the fingers and thumb as well as the amount of pressure applied to the fingers and thumb may be controlled. The controlled manipulation of the fingers and thumb enables a therapist to create customized treatments for treating the metacarpal and phalangeal joints in the affected hand. This displacement of the fingers and thumb assists with passive flexion and extension of the metacarpal and phalangeal joints for the affected hand.

The method 200 may include an initial Step 202 of applying a therapeutic pain relief modality to an affected hand. The affected hand is treated through pain relief modality, which may include, without limitation, heat, paraffin, myofascial release, hot or ice packs, and gently stretching. The pain relief modality is applied before receiving the therapeutic benefits of the glove 102.

The method 200 may further comprise a Step 204 of providing a therapeutic glove 102, the therapeutic glove 102 configured to adjustably apply passive flexion and extension of metacarpal and phalangeal joints of the affected hand. The glove 102 comprises a body portion 104 that is configured to receive the affected hand. The body portion 104 includes a body dorsal side 106 and a body palm side 122. The glove 102 is resilient and dimensioned to fit a variety of affected hand sizes.

The glove 102, when donned, enables the fingers and thumb to be pulled and restrained in a first direction to form a flexion position. From the flexion position, the hand may grip an object and the metacarpal and phalangeal joints may be flexed in a therapeutic manner. Conversely, the glove 102 also enables the fingers and thumb to be pulled and restrained in a second direction to form an extension position. The extension position is efficacious for treating cramps.

A Step 206 includes passing the affected hand through an opening in a wrist portion 110 of the therapeutic glove 102. The wrist portion 110 enables passage of the affected hand. The wrist portion 110 includes a wrist dorsal side 112 and a wrist palm side 128. The wrist dorsal side 112 has a wrist dorsal fastener 114. The wrist dorsal fastener 114 is a strip of a hook and loop fastener. The wrist palm side 128 forms the opposite side to the wrist dorsal side 112. The wrist palm side 128 has a wrist palm fastener 130. The wrist palm fastener 130 is a strip of a hook and loop fastener.

In some embodiments, a Step 208 comprises engaging a plurality of fingers and a thumb in a plurality of tubular finger members. The tubular finger elements 116a-e that are configured to receive a plurality of digits and at least partially extend or flex the digits. The digits may include the four fingers and the thumb.

A Step 210 includes pulling a plurality of restraining members 118a-e in a first direction. Pulling the restraining members 118a-e in the first direction and joining the restraining member dorsal fastener 120 to the complimentary dorsal fasteners 108, 114 of the body portion 104 and wrist portion 110 forms a flexion position.

In some embodiments, a Step 212 may include detachably attaching a body dorsal fastener 108 and a wrist dorsal fastener 114 around a restraining member dorsal fastener 120 to form a flexion position. The flexion position enables the hand to grip an object and the metacarpal and phalangeal joints to flex. The amount of force applied while pulling the restraining members 118a-e dictates the pressure that is applied onto the metacarpal and phalangeal joints of the affected hand.

A Step 214 comprises pulling the plurality of restraining members 118a-e in a second direction. Pulling the restraining members 118a-e in the second direction and joining the restraining member palm fastener 132 to the complimentary palm fasteners 124, 130 of the body portion 104 and wrist portion 110 forms an extension position.

A final Step 216 includes detachably attaching a body palm fastener 124 and a wrist palm fastener 130 around a restraining member palm fastener 132 to form an extension position. The extension position enables the metacarpal and phalangeal joints of a hand to stretch. In one possible embodiment, therapeutic session with the glove 102 may be for no less than twenty minutes up to sixty minutes, and a recommended schedule is one or two times daily for these durations.

In conclusion, the therapeutic system 100 and method 200 provides a simple and efficient dynamic solution to patients with problems performing therapeutic exercises like passive flexion and extension of the fingers, effective grasping of utensils and therapeutic weights, or use of static and dynamic splints due to hemiplegia, hemiparesis, and others injuries limiting the normal performance of the hand.

Numerous citations describe the advantages of the present therapeutic system and method. Some of the studies are as follows:

Brunner, I. C., Skouen, J. S., & Strand, L. I. (2011). Recovery of upper extremity motor function post stroke with regard to eligibility for constraint-induced movement therapy. *Topics in Stroke Rehabilitation*, 18(3), 248-257

Frohlich, L., Wesley, A., Wallen, M., & Bundy, A. (2012). Effects of neoprene wrist/hand splints on handwriting for students with joint hypermobility syndrome: a single system design study. *Physical & Occupational Therapy in Pediatrics*, 32(3):243-255.

Han, C., Wang, Q., Meng, P., & Qi, M. (2013) Effects of intensity of arm training on hemiplegic upper extremity motor recovery in stroke patients: a randomized controlled trial. *Clinical Rehabilitation*, 27(1), 75-81

Khan, C. M, Oesh, P. R., Gamper, U. N., Kool, J., & Beer, S. (2012) Potential effectiveness of three different treatment approaches to improve minimal to moderate arm and hand function after stroke. *Clinical Rehabilitation*, 26(8), 758-60.

Vannajak, K., Boonprakob, Y., Eungpinichpong, W., Ungpansattawong, S., Nanagara, R. (2014). The short term effect of gloving in combination with Traditional Thai Massage, heat, and stretching exercise to improve hand mobility in scleroderma patients. *Journal of Ayurveda & Integrative Medicine*, 5(1), 50-55

Waller, S. M., Whitall, J., Jenkins, T., Magder, L. S., Hanley, D. F., Goldberg, A., & Luft, A. R. (2014). Sequencing bilateral and unilateral task oriented training alone to improve arm function in individuals with chronic stroke. *BMC Neurology*, 14(1), 106-124

Workout for aching hands (2010). *Harvard Women's Health Watch*, 18(2), 2-3.

While the inventor's above description contains many specificities, these should not be construed as limitations on the scope, but rather as an exemplification of several preferred embodiments thereof. Many other variations are possible. For example, the plurality of tubular finger elements can be pulled in a lateral direction, rather than in the first (forward) and second (backward) directions. Accordingly, the scope should be determined not by the embodiments illustrated, but by the appended claims and their legal equivalents.

What is claimed is:

1. A therapeutic system and device for flexing and extending the metacarpal and phalangeal joints of a hand, the system comprises:
    a glove, the glove comprising a body portion having a body dorsal side and a body palm side, the body dorsal side having a body dorsal fastener, the body palm side having a body palm fastener, the glove further comprising a wrist portion, the wrist portion having a wrist dorsal side and a wrist palm side, the wrist dorsal side having a wrist dorsal fastener, the wrist palm side having a wrist palm fastener, the glove further comprising a plurality of tubular finger elements, each tubular finger element configured to enable receiving and at least partially extending or flexing a digit; and
    a plurality of restraining members disposed to extend from the plurality of tubular finger elements, the plurality of restraining members comprising a restraining member dorsal fastener complimentary to the body dorsal fastener and the wrist dorsal fastener, the plurality of restraining members further comprising a restraining member palm fastener complimentary to the body palm fastener and the wrist palm fastener, wherein the complimentary dorsal fasteners join to form a flexion position when the plurality of restraining members are pulled in a first direction, and wherein the complimentary palm fasteners join to form an extension position when the plurality of restraining members are pulled in a second direction.

2. The system of claim 1, wherein the glove is configured to receive an affected hand for applying passive flexion and extension of the metacarpal and phalangeal joints of an affected hand.

3. The system of claim 2, wherein the flexion position is configured to grip an object and flex the metacarpal and phalangeal joints of the affected hand.

4. The system of claim 3, wherein the extension position is configured to stretch the metacarpal and phalangeal joints of the affected hand.

5. The system of claim 4, wherein the system includes a therapeutic pain relief modality adapted to be applied to the affected hand prior to the glove receiving the affected hand.

6. The system of claim 5, wherein the pain relief modality includes at least one member from the group consisting of: a paraffin, myofascial release, hot pack, an ice pack, and gentle stretching.

7. The system of claim 1, wherein the glove includes at least one member from the group consisting of: small size, medium size, and large size.

8. The system of claim 1, wherein the body dorsal fastener and the body palm fastener include panels of a hook and loop fastener about six inches wide and two inches long.

9. The system of claim 1, further including a leather padding configured to hingedly cover the body palm fastener.

10. The system of claim 1, wherein the wrist portion comprises a wrist strap having a wrist palm fastener for securing the glove around a wrist.

11. The system of claim 1, wherein the wrist portion has an opening configured to enable passage of a hand.

12. The system of claim 1, wherein the wrist dorsal fastener is a strip of a hook and loop fastener about four inches long and two inches wide.

13. The system of claim 1, wherein the wrist palm fastener is a strip of a hook and loop fastener about four inches long and two inches wide.

14. The system of claim 1, wherein the plurality of tubular finger members include five tubular finger members configured to receive four fingers and one thumb.

15. The system of claim 1, wherein the plurality of restraining members are configured to extend from the termini of the plurality of tubular finger elements.

16. The system of claim 1, wherein the restraining member dorsal fastener is a strip of a hook and loop fastener about six inches long and half an inch wide.

17. The system of claim 1, wherein the system further comprises a secondary glove configured to receive an unaffected hand, the secondary glove further configured to enable a user to compensate the tactile perception feedback from the unaffected hand.

18. The system of claim 1, wherein the system is adapted to be utilized between twenty to sixty minutes, and one time to two times daily.

19. The system of claim 1, wherein the glove is fabricated from a resilient material.

\* \* \* \* \*